United States Patent [19]

Suami

[11] 4,157,439
[45] Jun. 5, 1979

[54] NOVEL NITROSOUREA DERIVATIVES

[76] Inventor: Tetsuo Suami, 5-8, Nakacho 3-chome, Musashino-shi, Tokyo, Japan

[21] Appl. No.: 828,099

[22] Filed: Aug. 26, 1977

[30] Foreign Application Priority Data

Sep. 2, 1976 [JP] Japan .................. 51-104300

[51] Int. Cl.$^2$ .............. C07H 19/00; A61K 31/70
[52] U.S. Cl. ................... 536/22; 424/180; 536/18; 536/53
[58] Field of Search ............... 536/22, 53; 424/180

[56] References Cited

U.S. PATENT DOCUMENTS

| 3,577,406 | 5/1971 | Hessler | 536/53 |
| 4,022,963 | 5/1977 | Deutsh | 536/22 |

Primary Examiner—Johnnie R. Brown
Assistant Examiner—Blondel Hazel
Attorney, Agent, or Firm—Larson, Taylor and Hinds

[57] ABSTRACT

Novel nitrosourea derivatives are provided which possess a high inhibitory activity against the leukemia and tumors with a low toxicity and a good stability against humidity and which are useful for pharmaceutical purposes. The compounds have the structure:

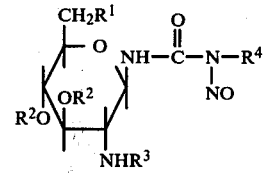

wherein $R^1$ represents hydroxyl or alkanoyloxy containing 2-4 carbon atoms; $R^2$ represents hydrogen or alkanoyl containing 2-4 carbon atoms; $R^3$ represents alkanoyl containing 2-4 carbon atoms; and $R^4$ represents alkyl or halo-substituted alkyl containing 1-4 carbon atoms.

8 Claims, No Drawings

NOVEL NITROSOUREA DERIVATIVES

BACKGROUND OF THE INVENTION

This invention relates to novel nitrosourea derivatives which exhibit a high level of activity against the leukemia and tumors with a low toxicity and a good stability against humidity and which are therefore useful in the therapeutic treatments of the leukemia and tumors. This invention further relates to a process for the preparation of such novel nitrosourea derivatives and to their use for pharmaceutical purposes.

There are a variety of compounds which have been proposed as being effective for inhibiting the leukemia and tumors and one class of which is nitrosourea derivatives. Among the nitrosourea derivatives, there may be mentioned Streptozotocin [N-(N'-methyl-N'-nitrosocarbamoyl)-D-glucosamine] and their derivatives such as methyl glucosaminides as most typical examples, but they are not satisfactory yet because of insufficient activity against the leukemia and tumors and/or undesirable side effect thereof. Another class of the nitrosourea derivatives is glycosyl derivatives of nitrosoureas which I have most recently proposed, of which the most preferred example is 1-(2-chloroethyl)-3-(β-D-glucopyranosyl)-1-nitrosourea which was found to have a remarkably high inhibitory activity against a variety of leukemia and tumors with a low toxicity and a low side effect, but to be somewhat hygroscopic.

I have now found that certain novel nitrosourea derivatives, as hereinafter defined, exhibit a high inhibitory activity against the leukemia and tumors with a low toxicity as evidenced by in vivo tests and has a good stability against humidity.

According to one aspect of this invention, therefore, there are provided as novel compounds nitrosourea derivatives of the formula:

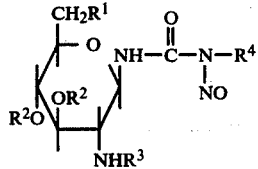

wherein $R^1$ represents a hydroxyl or an alkanoyloxy containing 2-4 carbon atoms; $R^2$ represents a hydrogen or an alkanoyl containing 2-4 carbon atoms; $R^3$ represents an alkanoyl containing 2-4 carbon atoms; and $R^4$ represents an alkyl containing 1-4 carbon atoms or a halo-substituted alkyl containing 1-4 carbon atoms.

DETAILED DESCRIPTION OF THE INVENTION

As examples of the nitrosourea compounds of the formula (I), there may be enumerated those having, as the substituted glucopyranosyl group thereof, 2-acetamido-3,4,6-tri-O-acetyl-2-deoxy-β-D-glucopyranosyl, 2-acetamido-2-deoxy-β-D-glucopyranosyl, 2-deoxy-2-propionamido-3,4,6-tri-O-propionyl-β-D-glucopyranosyl, 2-deoxy-2-propionamido-β-D-glucopyranosyl, 2-deoxy-2-butyramido-3,4,6-tri-O-butyryl-β-D-glucopyranosyl and 2-deoxy-2-butyramido-β-D-glucopyranosyl. As the group $R^4$, there may be exemplified methyl, ethyl, propyl, i-propyl, butyl, i-butyl, sec-butyl, tert-butyl, chloromethyl, β-chloroethyl, β-chloropropyl, γ-chloropropyl, δ-chlorobutyl and β-bromoethyl.

Most typical nitrosourea derivatives of the formula (I) according to this invention include 1-(2-chloroethyl)-3-(2-acetamido-3,4,6-tri-O-acetyl-2-deoxy-β-D-glucopyranosyl)-1-nitrosourea and 1-(2-chloroethyl)-3-(2-acetamido-2-deoxy-β-D-glucopyranosyl)-1-nitrosourea.

The novel nitrosourea derivatives of the formula (I) according to this invention may be prepared simply by nitrosating the corresponding urea derivative in a known manner per se.

According to another aspect of this invention, therefore, there is provided a process for the preparation of nitrosourea derivative of the formula:

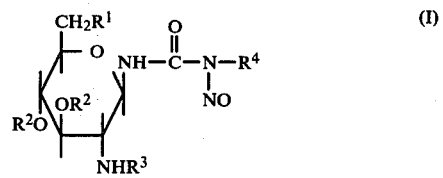

wherein $R^1$, $R^2$, $R^3$ and $R^4$ have the same meanings as defined above which comprises treating a compound of the formula:

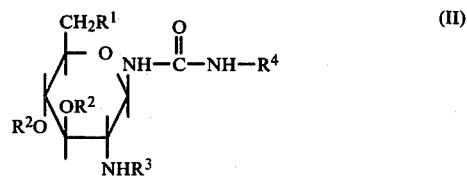

wherein $R^1$, $R^2$, $R^3$ and $R^4$ have the same meanings as defined above with a nitrosating agent.

In the process of this invention, the nitrosation reaction may be carried out in a known manner per se by using as nitrosating agent an alkali metal nitrite, nitrogen trioxide, dinitrogen tetroxide and the like. As alkali metal nitrite, sodium or potassium nitrite is preferred. The nitrosation reaction may usually be conducted at a temperature of about $-10°$ C. to $30°$ C. and preferably under an acidic condition, for example, at a pH value of about 1 to 3. The use as reaction medium of an organic acid such as formic and acetic acids is suitable. Under these conditions, the reaction time is suitably about 1 to 12 hours. After the completion of the nitrosation reaction, the reaction mixture is poured into ice water to deposit the desired nitrosourea as crude crystals. Purification of the product can be effected by recrystallization from a suitable solvent. In cases where nitrogen trioxide or dinitrogen tetroxide is used as nitrosating agent, it is preferred to use such a gaseous nitrosating agent in the form of a solution in formic acid or acetic acid or by bubbling it as such into a solution of the starting compound in a solvent such as formic or acetic acid.

Alternatively, the nitrosourea derivatives of the formula (I) according to this invention may be prepared by alkanoylating the corresponding nitrosourea derivative having free OH groups on its glucopyranosyl moiety in a known manner per se.

According to a further aspect of this invention, therefore, there is provided a process for the preparation of nitrosourea derivative of the formula:

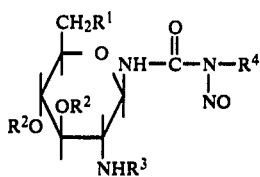

wherein $R^1$ represents an alkanoyloxy containing 2–4 carbon atoms, $R^2$ represents an alkanoyl containing 2–4 carbon atoms provided that $R^2O$ is the same as $R^1$ and $R^3$ and $R^4$ have the same meanings as defined above which comprises alkanoylating a nitrosourea compound of the formula:

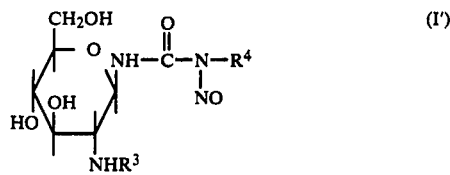

wherein $R^3$ and $R^4$ have the same meanings as defined above with an alkanoylating agent.

As alkanoylating agent, there may be used an acid anhydride or acid halide such as acetic anhydride, propianic anhydride, butyric anhydride, acetyl chloride, propionyl chloride and butyryl chloride. The reaction is preferably carried out in a basic solvent such as pyridine, usually at 0–50° C. for 4–48 hours. After the completion of the reaction, the reaction mixture is poured into ice water to deposit crude nitrosourea derivative thus produced. Purification may be effected by recrystallization from a suitable solvent.

The novel nitrosourea derivatives of the formula (I) according to this invention have been confirmed in vivo tests to exhibit a high level of inhibitory activity against the leukemia and tumors with a low toxicity and a high stability against humidity.

According to a further important aspect of this invention, therefore, there is provided a pharmaceutical composition comprising an effective amount of a nitrosourea derivative of the formula (I) in association with a pharmaceutically acceptable excipient, carrier or diluent.

The pharmaceutical composition may be in a form known per se to suit the route of administration, that is oral, injection or intraperitoneal administration for animals. In general, therefore, the pharmaceutical composition may take such form as ampoule, capsule, tablet, powder, granule and the like to adapt oral or injection administration.

This invention also includes within its scope a method for the therapeutic treatment of leukemic and tumor diseases in animals which comprises administering to the animal a therapeutically effective amount, at suitable intervals, of a nitrosourea derivative of the formula (I) above. It will be appreciated that the amount to be actually applied of the nitrosourea derivative will vary dependent upon the particular compound used, the particular composition formulated, the mode of application, the route of administration and others. Many factors which modify the action of the drug will be taken into account by the skilled in the art, for example, age, body weight, sex, diet, time of administration, route of adminstration, rate of metabolism or excretion, drug combination, sensitivities and severity or condition of the disease. Optimal application dose for a given set of conditions can be ascertained by the skilled in the art using conventional tests for the dosage determination in view of the above guidelines.

The anti-leukemic activity of some typical nitrosourea derivatives of the formula (I) according to this invention was tested on Leukemia L 1210 in mice, details of which are given below. By way of comparison, Streptozotocin was tested in the same way.

Compounds

| Compound No. | Name |
|---|---|
| 1 | 1-(2-Chloroethyl)-3-(2-acetamido-3,4,6-tri-O-acetyl-2-deoxy-$\beta$-D-glucopyranosyl)-1-nitrosourea |
| 2 | 1-(2-Chloroethyl)-3-(2-acetamido-2-deoxy-$\beta$-D-glucopyranosyl)-1-nitrosourea |
| 3 | Streptozotocin (Reference) |

Animals

Male $BDF_1$ mice, aging about 6-weeks old and weighing 22±1 g were used in groups of 5 animals each for the tests.

Methods

Each animal was inoculated with $10^6$ cells of L 1210 intraperitoneally, and the test compound in the form as shown below was administered intraperitoneally from the 24th hour after inoculation once a day for 3 consecutive days. The anti-leukemic activity was assessed by comparing the mean survival days of the treated mice to that of the untreated control, i.e. percentage increase in life-span (ILS) which was calculated as follows:

Percentage increase in life-span $(ILS) = (T - C/C) \times 100$

T: The mean survival days of the treated animals
C: The mean survival days of the untreated animals The compounds No. 1 and No. 3 were used in the form of an aqueous solution in distilled water and the compound No. 2 in the form of an aqueous suspension containing 1% CMC.

The test results are shown in Table 1.

Table 1

Anti-leukemic activity of nitrosourea derivatives
(60 days observation)

| Compound No. | Dose (mg/kg) | Survival days | ILS (%) | Number of survivors (after 60 days) |
|---|---|---|---|---|
| 1 | 8 | 16.4 | 105.0 | 0/5 |
|   | 4 | 14.3 | 78.8 | 0/5 |
| 2 | 8 | <47.6 | <495.0 | 3/5 |
|   | 4 | 15.6 | 95.0 | 0/5 |
|   | 2 | 12.4 | 55.0 | 0/5 |
|   | 1 | 11.3 | 41.3 | 0/5 |
| 3 | 100 | 10.6 | 32.5 | 0/5 |
|   | 50 | 12.1 | 51.3 | 0/5 |
| Untreated (control) |  | 8.0 | — | 0/5 |

It will be appreciated clearly from the tests results of Table 1 that the novel nitrosourea derivatives according to this invention gave a significant increase in life-span in therapeutic treatment of the leukemia in comparison with streptozotocin as a known anti-leukemic nitrosourea. The novel nitrosourea derivatives according to this invention are further characterized by their low toxicity, thus satisfying their practical application for treating leukemia and tumor diseases. For example, acute toxicity in the intraperitoneal administration to BDF$_1$ mice of typical nitrosourea derivatives according to this invention is shown below:

| | LD$_{50}$ |
|---|---|
| 1-(2-Chloroethyl)-3-(2-acetamido-3,4,6-tri-O-acetyl-2-deoxy-β-D-glucopyranosyl)-1-nitrosourea | 25 mg/kg |
| 1-(2-Chloroethyl)-3-(2-acetamido-2-deoxy-β-D-glucopyranosyl)-1-nitrosourea | 20 mg/kg |

This invention is illustrated, by way of example only, by the following Examples in which are also included steps for the preparation of the starting compounds.

EXAMPLE 1

(a) Preparation of 2-acetamido-3,4,6-tri-O-acetyl-2-deoxy-β-D-glucopyranosylazide 2-Acetamido-3,4,6-tri-O-acetyl-2-deoxy-α-D-glucopyranosyl chloride (1.0 g) which was prepared by the method proposed by R. L. Whistler et al. [Methods in Carbohydrate Chem. VI, 284–285 (1972)] was dissolved in acetonitrile (10 ml). Sodium azide (1.2 g) was added to the solution and the mixture was heated under reflux on an oil bath maintained at 90° C. for 18 hours and allowed to cool to ambient temperature and then filtered to remove insoluble matters. On concentrating the filtrate under a reduced pressure, there deposited crude crystals of the titled compound. Yield 0.86 g (84%). mp. 170°–171° C. $[\alpha]_D^{22}$ −48° (c 1.09, chloroform).

Elementary analysis: C$_{14}$H$_{20}$N$_4$O$_8$ requires: C, 45.16; H, 5.41; N, 15.05%. Found: C, 45.29; H, 5.34; N, 15.17%.

(b) Preparation of 2-acetamido-3,4,6-tri-O-acetyl-2-deoxy-β-D-glucopyranosylamine The azide derivative (1.0 g) obtained in the step (a) above was dissolved in methanol (10 ml) and the resulting solution was subjected to catalytic hydrogenation under the hydrogen pressure of 3.4 kg/cm$^2$ in the presence of Raney nickel and then concentrated to obtain crude crystals of the titled compound. Yield 0.69 g (74%). Recrystallization from ethanol gave the product in pure state. mp. 143°–145° C. (with decomposition). $[\alpha]_D^{20}$ −16° (c 1.12, chloroform).

Elementary analysis: C$_{14}$H$_{22}$N$_2$O$_8$ requires: C, 48.55; H, 6.46; N, 8.09%. Found: C, 48.65; H, 6.33; N, 7.98%.

(c) Preparation of 1-(2-chloroethyl)-3-(2-acetamido-3,4,6-tri-O-acetyl-2-deoxy-β-D-glucopyranosyl) urea The amino derivative (280 mg) obtained in the step (b) above was dissolved in methanol (4 ml), to which was then added 2-chloroethylisocyanate (0.1 ml) under ice-cooling. The reaction was carried out at room temperature for 16 hours, during which precipitation occurred. The precipitate was filtered off as a first crop of the desired product. The filtrate was concentrated under a reduced pressure and the residue was crystallized from ethanol to obtain crude crystals as a second crop of the product. The total yield of the product was 370 mg (quantitative).

Recrystallization from ethanol gave 280 mg (76%) of the titled compound in a pure state. mp. 226°–227° C. (with decomposition). $[\alpha]_D^{19}$ +0.7° (c 1.05, methanol).

Elementary analysis: C$_{17}$H$_{26}$N$_3$ClO$_9$ requires: C, 45.19; H, 5.80; N, 9.30; Cl, 7.85%. Found: C, 45,08; H, 5.69; N, 9.28; Cl, 7.77%.

(d) Preparation of 1-(2-chloroethyl)-3-(2-acetamido-2-deoxy-β-D-glucopyranosyl) urea The triacetate derivative (260 mg) obtained in the step (c) above was dissolved in methanol (15 ml) which had been saturated with ammonia gas, and the mixture was allowed to stand at room temperature for 3 hours. Concentration of the reaction solution under a reduced pressure followed by recrystallization of the concentrated residue from ethanol gave the titled compound. Yield 170 mg (90%). mp. 181°–182° C.

Elementary analysis: C$_{11}$H$_{20}$N$_3$ClO$_6$ requires: C, 40.56; H, 6.19; N, 12.90; Cl, 10.88%. Found: C, 40.17; H, 6.07; N, 12.76; Cl, 10.64%.

(e) Preparation of 1-(2-chloroethyl)-1-nitroso-3-(2-acetamido-2-deoxy-β-D-glucopyranosyl) urea 1-(2-Chloroethyl)-3-(2-acetamido-2-deoxy-β-D-glucopyranosyl) urea (1.0 g) which was obtained as in the step (d) above was dissolved in 99% formic acid (2.5 ml), to which was then added sodium nitrite (0.32 g) under stirring and ice-cooling. After one hour, the reaction mixture was diluted with the addition of ethylether. Supernatant liquid layer was removed to leave oily deposits which were then washed with ethylether several times and the remaining solid mass was dissolved in ethanol (40 ml). The resulting solution was filtered and the filtrate was treated with a cation exchange resin "Amberlite" IR-120 (H$^+$ form) (Amberlite is a trade name). The filtrate was then concentrated under a reduced pressure and the residue was recrystallized from acetone to afford the titled compound as pale yellow crystals. Yield 0.44 g (40%). mp. 159–162° C. (with decomposition). $[\alpha]_D^{19}$ −39° (c 1.0, methanol).

Elementary analysis: C$_{11}$H$_{19}$N$_4$ClO$_7$ requires: C, 37.24; H, 5.40; N, 15.79; Cl, 9.99%. Found: C, 37.15; H, 5.41; N, 15.57; Cl, 9.90%.

EXAMPLE 2

Preparation of 1-(2-chloroethyl)-1-nitroso-3-(2-acetamido-3,4,6-tri-O-acetyl-2-deoxy-β-D-glucopyranosyl) urea (1) 1-(2-Chloroethyl)-3-(2-acetamido-3,4,6-tri-O-acetyl-2-deoxy-β-D-glucopyranosyl) urea (1.0 g) which was obtained as in the step (c) of Example 1 above was dissolved in 99% formic acid (2.5 ml), to which was then added sodium nitrite (0.46 g) under stirring and ice-cooling. After continuing the stirring for 90 minutes, the reaction mixture was poured into ice water to deposit crystals. After filtration, the titled compound was obtained as pale yellow crystals. Yield 0.75 g (70%). $[\alpha]_D^{19}$ −31° (C 1.0, acetone).

Elementary analysis: C$_{17}$H$_{25}$N$_4$ClO$_{10}$ requires: C, 42.46; H, 5.24; N, 11.65; Cl, 7.37%. Found: C, 42.46; H, 5.15; N, 11.75; Cl, 7.51%.

(2) 1-(2-Chloroethyl)-1-nitroso-3-(2-acetamido-2-deoxy-β-D-glucopyranosyl) urea (1.0 g) which was obtained as in the step (e) of Example 1 above was acetylated with acetic anhydride (6 ml) in pyridine (6 ml). The reaction mixture was concentrated under a reduced pressure and the residue was recrystallized from ethanol to afford the titled compound. Yield 1.09 g (78%). The result of elementary analysis of this compound coincided with that given in (1) above.

What I claim is:

1. Nitrosourea derivative of the formula:

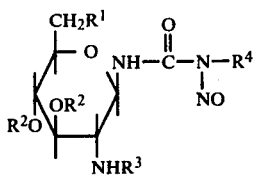 (I)

wherein R[1] represents a hydroxyl or an alkanoyloxy containing 2–4 carbon atoms; R[2] represents a hydrogen or an alkanoyl containing 2–4 carbon atoms; R[3] represents an alkanoyl containing 2–4 carbon atoms; and R[4] represents a halo-substituted alkyl containing 1–4 carbon atoms.

2. Nitrosourea derivative as claimed in claim 1 wherein R[1] represents a hydroxyl or acetyloxy.

3. Nitrosourea derivative as claimed in claim 1 wherein R[2] represents a hydrogen or acetyl.

4. Nitrosourea derivative as claimed in claim 1 wherein R[3] represents an acetyl.

5. Nitrosourea derivative as claimed in claim 1 wherein R[4] represents a chloro-substituted alkyl containing 1–4 carbon atoms.

6. Nitrosourea derivative as claimed in claim 5 wherein R[4] represents β-chloroethyl.

7. 1-(2-Chloroethyl)-1-nitroso-3-(2-acetamido-2-deoxy-β-D-glucopyranosyl) urea.

8. 1-(2-Chloroethyl)-1-nitroso-3-(2-acetamido-3,4,6-tri-O-acetyl-2-deoxy-β-D-glucopyranosyl) urea.

* * * * *